United States Patent
Kliman

(10) Patent No.: US 9,504,442 B2
(45) Date of Patent: Nov. 29, 2016

(54) METHOD AND SYSTEM FOR DETERMINING PLACENTAL VOLUME

(76) Inventor: Harvey Kliman, Woodbridge, CT (US)

( * ) Notice: Subject to any disclaimer, the term of this patent is extended or adjusted under 35 U.S.C. 154(b) by 1111 days.

(21) Appl. No.: 12/524,569

(22) PCT Filed: Feb. 1, 2008

(86) PCT No.: PCT/US2008/001373
§ 371 (c)(1),
(2), (4) Date: Jul. 25, 2009

(87) PCT Pub. No.: WO2008/097475
PCT Pub. Date: Aug. 14, 2008

(65) Prior Publication Data
US 2009/0326376 A1    Dec. 31, 2009

Related U.S. Application Data

(60) Provisional application No. 60/899,282, filed on Feb. 2, 2007.

(51) Int. Cl.
*A61B 8/08* (2006.01)
*G06T 7/00* (2006.01)
*G06T 7/60* (2006.01)

(52) U.S. Cl.
CPC ............... *A61B 8/08* (2013.01); *G06T 7/0012* (2013.01); *G06T 7/602* (2013.01); *G06T 2207/10132* (2013.01); *G06T 2207/30044* (2013.01)

(58) Field of Classification Search
CPC ........ A61B 8/08; G06T 7/0012; G06T 7/602
USPC ................ 600/437, 438, 443; 128/898, 916; 382/128, 154
See application file for complete search history.

(56) References Cited

U.S. PATENT DOCUMENTS

2007/0004983 A1*   1/2007   Chalana et al. .............. 600/443

OTHER PUBLICATIONS

Hafner et al. "Comparison between three-dimensional placental volume at 12 weeks and uterine artery impedance/notching at 22 weeks in screening for pregnancy-induced hypertension, pre-eclampsia and fetal growth restriction i a low-risk population", Ultrasound Obstetrics and Gynecology, vol. 27, pp. 652-57, 2006.*
Thame et al., "Fetal growth is directly related to maternal anthropometry and placental volume", European Journal of Clinical Nutrition, vol. 58, pp. 894-900, 2004.*

(Continued)

*Primary Examiner* — Joseph M Santos Rodriguez
(74) *Attorney, Agent, or Firm* — Renner, Otto, Boisselle and Sklar, LLP

(57) ABSTRACT

Method and system for determining a volume of a placenta in utero. The placenta in utero may be modeled as having a convex-concave shape (e.g., like that of a portion of a spherical shell). Volume of the placenta may be determined based on the width (or height) and thickness of the placenta, or based on width, height and thickness of the placenta. Placenta size characteristics may be measured using imaging techniques, such as ultrasound. In one aspect of the invention, a volume of a placenta in utero may be compared to the volume of other placentas for similar gestational age, and a determination regarding whether the placenta volume poses a risk to fetal health may be made.

17 Claims, 4 Drawing Sheets

(56) References Cited

OTHER PUBLICATIONS

Habib, "Prediction of low birth weight infants from ultrasound measurement of placental diameter and placental thickness", Annals of Soudi Medicine, vol. 22(5-6), pp. 312-314, 2002.*

Wegrzyn et al., "Placental volume measured by three-dimensional ultrasound at 11 to 13+6 weeks of gestation: relation to chromosomal defects", vol. 26, pp. 28-32, 2005.*

De Odorico et al. "Normal Splenic Volumes Estimated Using Three-Dimensional ultrasonography", Journal Ultrasound Medicine vol. 18, p. 231-236, 1999.*

\* cited by examiner

METHOD AND SYSTEM FOR DETERMINING PLACENTAL VOLUME

This application claims the benefit of U.S. Provisional Application No. 60/899,282 filed Feb. 2, 2007.

BACKGROUND

1. Field of Invention

This invention relates to determining placental volume.

2. Related Art

A healthy placenta is an important factor in producing a healthy baby. The placenta makes hormones which control the basic physiology of the mother so that the fetus is supplied with necessary nutrients and oxygen needed for successful growth. The placenta also protects the fetus from immune attack by the mother, removes waste products from the fetus, induces the mother to bring more blood to the placenta, and near the time of delivery, produces hormones that mature the fetal organs in preparation for life outside the uterus.

One serious pathologic condition that can affect the health of a fetus is a small-for-gestational-age placenta. When there is inadequate placental mass, the fetus may be starved of nutrients and other substances needed to support normal fetal growth. Although the placenta can often compensate for a reduced placental mass, there often comes a point where the placenta is too small to sustain fetal life. Unfortunately, there is often no warning as to when this crisis might culminate in fetal demise. Also, a fetus may develop relatively normally right up until a time at which the small placental mass fails to adequately support the fetus. Thus, the fetus may appear perfectly healthy, yet be on the verge of death.

SUMMARY OF INVENTION

The inventor has appreciated that determining placental volume (and/or mass) in utero can be a useful tool for predicting fetal health. For example, the inventor has determined that placental volume that is less than 1% of a normal placental volume at a gestational age of less than about 20 weeks correlates well with fetal demise. Thus, aspects of the invention that relate to determining placental volume can be used in the gestational period to monitor for potential problems related to small placenta.

In one aspect of the invention, the inventor has appreciated that the placenta has a convex-concave shape in utero. Thus, the placenta in utero is modeled to have a convex-concave shape (similar to the shape of a beanie cap or portion of a spherical shell) having a width, a height and a thickness. This is in contrast to other techniques which model the placenta as having a plano-convex shape (similar to the shape of portion of a cut orange or solid sphere). See Hellman, et al., "Ultrasonic studies on the volumetric growth of the human placenta," American Journal of Obstetrics & Gynecology, vol. 16(5), pp. 399-401. That is, the inventor has appreciated that, while a placenta removed from the uterus may be modeled, from a volume perspective, as a cylinder or plano-convex shape, a placenta in utero has a convex-concave shape. The width, height and thickness dimensions of the placenta may be measured, e.g., using ultrasonic imaging techniques commonly used to examine and measure a fetus in utero or other suitable techniques. The measured dimensions may then be used to determine the placental volume (and/or mass if the placental density is known or assumed).

In another aspect of the invention, the volume of a placenta may be determined using only two size characteristics, e.g., measured height and thickness of the placenta. This aspect of the invention may allow for greater ease in determining placenta volume since only two measurements may be made, and both thickness and height may, in some cases, be made using a same image of the placenta. As a result, an operator may not need to obtain multiple images of the placenta to determine its volume in utero.

In another aspect of the invention, a method for determining a volume of a placenta includes capturing image information of a placenta in utero, e.g., by ultrasonic imaging device, measuring at least two size characteristics of the placenta in utero based on the captured image information (such as the height, thickness and/or width of the placenta), and determining a volume of the placenta based on the at least two size characteristics by using a model of the placenta that characterizes the placenta as having a 3-dimensional convex-concave shape with a height and a thickness. The size characteristics of the placenta may be determined, for example, from a displayed ultrasound image of the placenta (or a portion thereof) with an operator selecting portions of the image that correspond to portions of the placenta in a way similar to that used for measuring fetal limb length and other dimensions. In one embodiment, the volume of the placenta is determined based only on a measured height, thickness and width for the placenta. In another embodiment, one of a plurality of different models for determining placenta volume may be selected, e.g., a model that most closely matches the physical shape of the placenta may be selected from among one or more other models and used to determine placenta volume. All of the models may assume a basic convex-concave shape, but vary in other ways, such as providing for a circular or elliptical shape at the base of the placenta, allow for a tapering thickness, etc.

In another aspect of the invention, a computerized system for determining a volume of a placenta includes an input module that inputs at least two size characteristics of a placenta in utero determined from captured image information. In one embodiment, the at least two size characteristics include a height and a thickness. The system may also include a volume determining module that determines a volume of the placenta based on the at least two size characteristics, and uses a model of the placenta that characterizes the placenta as having a convex-concave shape with a height and a thickness. The system may be a modular component that can be added (whether by software, hardware and/or a combination of the two) to an existing imaging device (such as an ultrasonic, CT, MRI, PET or other imaging device). In other embodiments, the system may be fully integrated into an imaging device or may be completely separate from an imaging system, e.g., part of a desktop computer that receives size characteristic information from an operator and determines placenta volume.

In another aspect of the invention, a method for assessing fetal health includes measuring at least two size characteristics of a placenta for a fetus in utero, determining a volume of the placenta based on the at least two size characteristics, comparing the volume of the placenta to a plurality of other placenta volumes for other fetuses at a similar gestational age, and determining whether the volume of the placenta poses a health risk for the fetus. In one embodiment, a determination that the placenta volume poses a health risk for the fetus may be made if the placenta volume is in a 10th percentile or less of placenta volumes for other fetuses of similar gestational age, is in a 5th percentile or less of placenta volumes for other fetuses of similar gestational age, is less than 1% of a normal placenta volume for a given gestational age, or is not at or sufficiently near a normal growth curve of placenta volume versus gestational age. If such a determination is made, the mother and fetus may be followed more closely, e.g., placenta volume may be checked every week or other suitable period, and/or treatment may be implemented.

These and other aspects of the invention will be apparent from the following description and claims.

BRIEF DESCRIPTION OF THE DRAWINGS

Aspects of the invention are described below with reference to the drawings in which like numerals reference like elements and wherein.

DETAILED DESCRIPTION

Aspects of the invention are described below with reference to illustrative embodiments, but it should be understood that aspects of the invention are not limited to the embodiments described. For example, embodiments are described below in which a placenta is modeled as having a convex-concave shape, and the volume of the placenta is determined based on measured values for the placenta's width, height and thickness. However, it should be appreciated that at least some aspects of the invention are not limited to modeling the placenta shape as convex-concave and/or determining placenta volume based on measured dimensions of width, height and/or thickness. For example, aspects of the invention related to predicting a future health of the fetus as it relates to placenta size are not limited to any particular method for determining placenta volume. Instead, placenta volume may be determined in other suitable ways, such as by 3-dimensional ultrasonic imaging techniques, the use of other shape models, multiple image integration techniques (such as B-mode parallel planimetric technique), and so on.

Figure 1:
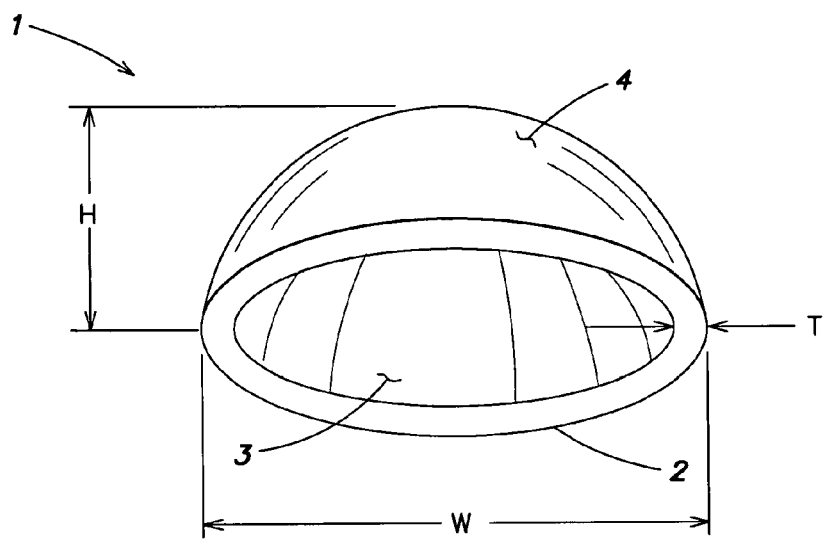
FIG. 1 shows a bottom perspective view of a model for the placenta having a convex-concave shape with a circular base and spherically-shaped inner and outer walls.

As shown in FIG. 1, in accordance with an aspect of the invention, a placenta in utero may be modeled as having a convex-concave shape, e.g., like that of a beanie cap. In one illustrative embodiment, a model 1 shown in FIG. 1 may have a circular shape at the base 2 and have the shape of a sphere at both the inner and outer walls 3 and 4, respectively, at all points above the base 2. In this example, the model 1 may have a width W, a height H and a thickness T. As shown in Equation 1 below, the volume of the placenta may be determined based on W, H and T:

$$V = \pi T \left[ \frac{W^2}{4} + H^2 - T \left( \frac{W^2}{8H} + \frac{3H}{2} - \frac{2T}{3} \right) \right] \qquad \text{Eqn. 1}$$

As will be appreciated, the model may be modified in any suitable way, thus resulting in different equations for determining the volume. For example, if the model 1 shown in FIG. 1 is assumed to have the shape of a hemispherical shell (where the width W is equal to the height H), Equation 2 below shows how the volume may be determined.

$$V = \pi T \left( \frac{W^2}{2} - WT + \frac{T^2}{3} \right) \qquad \text{Eqn. 2}$$

As can be seen in Equation 2 and in accordance with one aspect of the invention, the volume of the placenta may be determined based on only two measured parameters, in this case the width W (or height H since W=H) and the thickness T. Such an approach may simplify the process of determining the volume of a placenta in utero. For example, in some cases, the placenta's overall size and/or arrangement in the uterus may be larger than a display screen for an ultrasonic imaging device used to measure the placental dimensions. Thus, an operator may in some cases not be able to view the placenta width W dimension on a single image, making the measurement of the width W dimension difficult. However, use of a model like that described by Equation 2 may obviate the need to measure the width dimension.

In another illustrative embodiment, the model may assume a circularly shaped base 2 with an elliptical shape in the inner and outer walls 3 and 4 above the base 2 (i.e., an elliptical shape as seen in a vertical cross section of the shape shown in FIG. 1). Equation 3 may be used to determine placental volume using this model.

$$V = \frac{\pi T}{6} [4H(W - T) + W(W - 4T) + 4T^2] \qquad \text{Eqn. 3}$$

Figure 2:
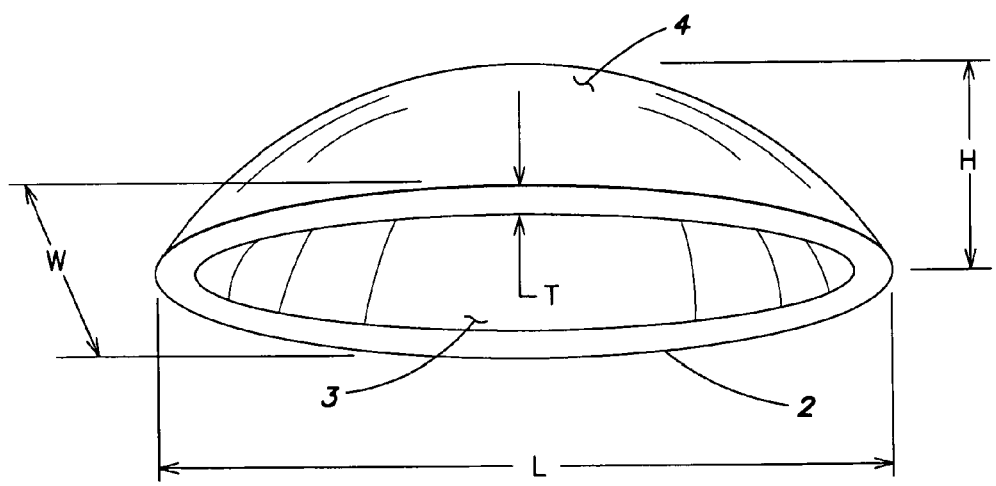
FIG. 2 shows a bottom perspective view of a model for the placenta having a convex-concave shape with an elliptical base and semi-elliptical shape in the inner and outer walls in vertical cross-section.

In another illustrative embodiment shown in FIG. 2, the model may assume an elliptical base 2 with the longest dimension at the base 2 being L and the shortest dimension at the base 2 being W and a semi-elliptical shape in the inner and outer walls 3 and 4 above the base 2 (as viewed in vertical cross section). Equation 4 may be used to determine placental volume using this model. This model may be useful in cases where the placenta is found to be somewhat elongated, rather than having a circular shape at the base 2.

$$V = \frac{\pi T}{6} \left[ 4H \left( \frac{L}{2} + \frac{W}{2} - T \right) + WL - 2LT - 2WT + 4T^2 \right] \qquad \text{Eqn. 4}$$

Figure 3:
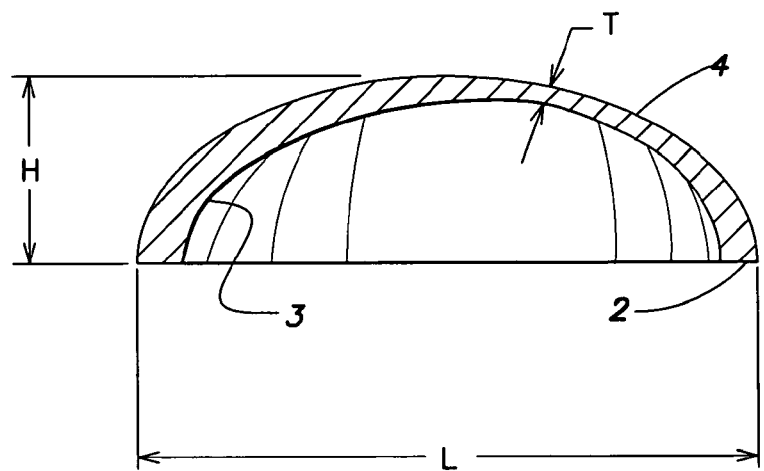
FIG. 3 shows a vertical cross-sectional view of a model for the placenta having a convex-concave shape with an elliptical base and semi-elliptical shape in the inner and outer walls in vertical cross-section and in which the wall thickness varies.

In another illustrative embodiment shown in FIG. 3, the model of FIG. 2 may be modified to account for a varying thickness T of the placenta where the model 1 has an elliptical shape at the base 2 and an elliptical shape of the inner and outer walls 3 and 4 above the base 2. In this model, the thickness of the placenta varies regularly and is defined as A*T, where A is a taper coefficient. If A is less than 1, the thickness T will taper to create thinner sides at the base 2. If A is greater than 1, the thickness T will taper to create thicker sides at the base 2. For example, if A=0.5, the thickness of the placental model at a point at the base 2 will be 50% of the thickness of the model at the extreme top of the model (where the maximum height H is achieved). As will be understood, if A=1, the model 1 is identical to that shown in FIG. 2 and represented in Equation 4. Equation 5 may be used to determine placental volume using this model.

$$V = \frac{\pi T}{6}[4HA(W - AT) + W(W - 4AT) + 4A^2T^2] \quad \text{Eqn. 5}$$

It should be understood that the models discussed above are only a few of the models that may be used to characterize a concave-convex placental shape for determining the placental volume. In short, aspects of the invention may include the use of any suitable model for a convex-concave shape, including models that account for regular and irregular variations in placenta thickness, width and/or height or other shape characteristics.

In accordance with one aspect of the invention, one of a plurality of different models may be selected to determine placental volume. For example, an operator, after observing the shape of a particular placenta using an ultrasound or other imaging device, may characterize the placenta as having a shape that most closely matches one of a plurality of different models, such as those discussed above. The selected model may then be used to determine placenta volume. In another embodiment, association of the placenta shape with one of a plurality of models may be done automatically, e.g., by an imaging system that analyzes one or more images of the placenta and selects a model that most closely represents the shape observed. Such association may involve the use of any suitable techniques, including image analysis, 3-dimensional modeling, and others. As a result, the placenta volume determination may take account of individual variations in placenta shape, choosing the most appropriate model to achieve the most accurate results possible.

In another aspect of the invention, a system for determining a volume of a placenta may include an input module that inputs two or more size characteristics of a placenta in utero, e.g., determined from captured image information. The two or more size characteristics may include a width, a height and/or a thickness of the placenta. The system may also include a volume determining module that determines a volume of the placenta based on the two or more size characteristics, using a model of the placenta that characterizes the placenta as having a convex-concave shape with a width, a height and/or a thickness.

Figure 4:
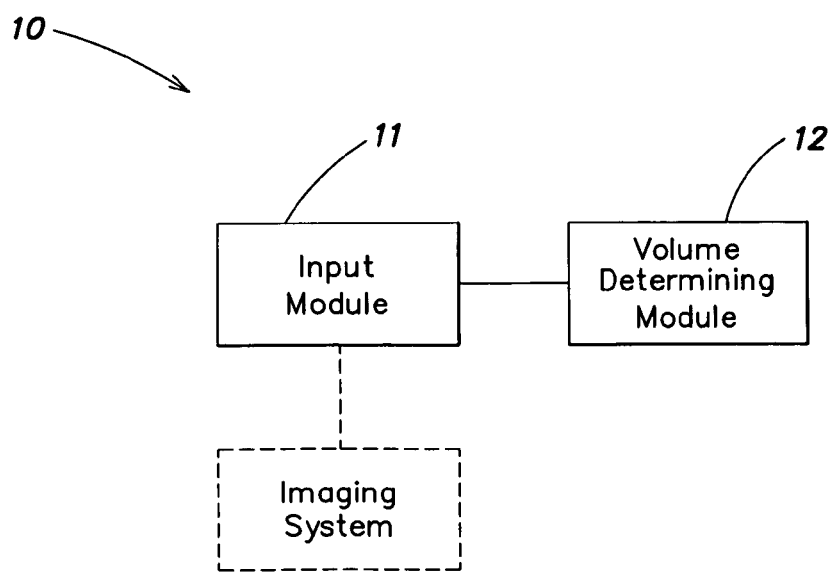
FIG. 4 shows schematic block diagram of a system for determining placenta volume.

FIG. 4 shows a schematic block diagram of a computerized system 10 that includes an input module 11 and a volume determining module 12 in an illustrative embodiment. The input module 11 may include any suitable components, such as an ultrasound imaging machine, X-ray imaging machine, MRI imaging device, CT imaging device and/or any other suitable device capable of acquiring at least a 2-dimensional image of the placenta. Such an imaging device may include a display screen (such as a CRT display, printer or other device) capable of generating an image observable by an operator. An operator may use one or more images captured by the imaging device to define two or more size characteristics of the placenta, such as width, height and/or thickness. For example, an operator may view an image of the placenta (or a portion of the placenta) on a display screen of the imaging device, and manipulate a user pointing device (such as a mouse, light pen, touch screen, etc.) to select regions on the image and thereby define the starting, intermediate, and/or end points for measuring the placenta size characteristics. Such techniques are widely used with ultrasonic imaging devices, e.g., for measuring various portions of a fetus. In other embodiments, the imaging device may automatically determine the size characteristics of the placenta by way of image analysis techniques or other means without the use of operator input (or using minimal operator input).

In yet another illustrative embodiment, the input module 11 need not include an imaging system at all, but rather may input size characteristic information in other ways. For example, an operator may input the width, height and/or thickness information by way of a keyboard or other user input device into a programmed general purpose computer that includes the input module 11. In one embodiment, the operator may obtain the size characteristics of the placenta by measurement on one or more printed images of the placenta, and provide the measured values to the input module 11 (e.g., by keyboard, voice input, etc.). In such a case, the input module 11 may include a software module or other set of computer code or instructions that cause the computer to perform functions associated with the input module 11, e.g., generate and display a graphical user interface (GUI) for the operator and receive and store the size characteristic information via the GUI. In another embodiment, the input module 11 may input size characteristic information from an imaging system, e.g., the input module 11 may be included with a general purpose or other computer and receive size information by a wired or wireless link from an ultrasound or other imaging device used to image the placenta and generate width, height, thickness and/or other measurements. In such a case, the input module 11 may include software, hardware and/or other components used to perform the function of the input module 11, e.g., receive and/or send communications with respect to the imaging system so as to ultimately input the size characteristic information (or information otherwise representative of the size characteristics). For example, the input module 11 may receive width, height and/or thickness information directly from the imaging system, or alternately, may receive image information from the imaging device so that the input module 11 can process the image information (e.g., via image analysis) to obtain the size characteristic information.

The volume determining module 12 may include one or more software modules, computer code or other instructions used by a computer to that determines a volume of the placenta based on the two or more size characteristics, using a model of the placenta that characterizes the placenta as having a convex-concave shape with a width, a height and/or a thickness. The "computer" may be a general purpose programmable computer, e.g., a desktop or laptop computer, that also includes the input module 11. Alternately, the volume determining module 12 may be included as part of an imaging device that has the capability to image the placenta, determine size characteristics (whether with or without user input) and determine the volume using the size characteristics. The volume determining module 12 may have the capability to analyze image information regarding the placenta and associate a particular volume model to the placenta's shape. The volume determining module 12 may choose one from a plurality of models based on user input (e.g., using a GUI) and/or perform the model selection automatically. It is also possible for the input module 11 and the volume determining module 12 to be implemented in a network environment, whether wired or wireless or a combination, and may include networks of various types, such as adhoc, WLAN, enterprise and other networks as well as the Internet. In another embodiment, the input module 11 and the volume determining module 12 may be implemented in an ASIC, programmed FPGA and/or other hardware or firmware arrangement, e.g., in a stand alone box or card that is associated an imaging system by installing the box or card in or on the imaging system. Thus, the system 10 may be arranged as a add-on module for an imaging system to provide an existing imaging system with capabilities in accordance with aspects of the invention.

In accordance with another aspect of the invention, a patient may be examined during pregnancy to determine the volume of the patient's placenta and predict whether complications due to placenta size may occur. For example, a patient may be examined at one or more times before and/or after 20-24 weeks gestation and the placenta size assessed against an average or normal placenta size for gestational age. Based on the comparison(s) between the patient's placenta and those of others of similar gestational age, a determination may be made whether the placenta size poses a risk to the health of the fetus. In one embodiment, if the placenta size is found to be in the $10^{th}$ percentile or less of a group of placenta volumes for fetuses of suitably similar gestational age, a conclusion may be made that there is a potential for fetal death (intrauterine fetal death or IUFD), and that the patient should be followed more closely and/or treatment administered. In another embodiment, if the placenta size is in the $5^{th}$ percentile or less, a conclusion may be reached that the mother and fetus be monitored closely and/or treatment administered. Other criteria may be used to determine whether the placenta is relatively small as compared to a normal placenta or group of other placentas for fetuses of similar gestational age. For example, in another embodiment, if the placenta volume is found to be less than 1% of average or normal size, the fetus and/or mother may be determined to be potentially at risk.

While small placenta size can present complications, very large placenta size can also pose a risk to fetal health. For example, large placental size may correlate with other potentially undetected problems, such as diabetes, syphilis infection, and/or Rh incompatibility. As those of skill in the art will appreciate, gestational or other forms of diabetes can result in a large-for-gestational-age fetus and placenta, which can cause problems during delivery and/or adversely affect the health of the mother and baby. Likewise, syphilis infection and Rh incompatibility can pose risks for mother and child, and identification of a very large placenta can be an indicator of a potentially problematic medical condition. In some cases, very small or very large placenta can be secondary to genetic abnormalities, e.g., chromosomal and/or nucleotide, and may be a first indicator of such a problem. Accordingly, at least one aspect of the invention may include assessing the placenta volume for large size alone, or for both large and small size. Based on the finding, intervention may be undertaken (e.g., including bed rest, increased fluids intake, administration of drugs, surgery, and/or other suitable treatment), and followed by subsequent evaluation of the results of treatment.

Various techniques may be used to compare a placenta's volume to the volumes of other placentas of similar gestational age. (Placentas of similar gestational age may include placentas associated with fetuses that grew to and/or near full term with successful delivery, placentas associated with fetuses that suffered IUFD or other complications, and/or placentas associated with other suitable fetus conditions.) For example, the volume of a placenta of interest may be determined at two or more different gestational ages, and the placenta volumes may be compared to a normal growth curve for a placenta. If the placenta is found to be suitably following the normal growth curve, a determination may be made that the fetus is not at risk of death or other complication, even though the placenta may be smaller than normal in some cases. On the other hand, if the placenta is found to be deviating from the normal growth curve, a determination may be made that the fetus and placenta should be watched closely. This may be true even if the placenta is at or above normal volume for gestational age. The growth curve used in such a comparison may be derived in any suitable way, such as by determining an average placenta volume for a plurality of fetuses at a plurality of different gestational ages. The curve formed by the average placenta volumes versus gestational age may be used as the normal growth curve. In another embodiment, the placenta volume may be compared to the volume of other placentas associated with fetuses that suffered IUFD or other complication. If the placenta volume is found to be sufficiently similar to the other placenta volumes, a determination may be made that the placenta size poses a health risk and treatment may be undertaken. Other techniques for comparing a particular patient's placenta volume to the volumes of other placentas of similar gestational age may be used, as will be apparent to those of skill in the art.

Figure 5:
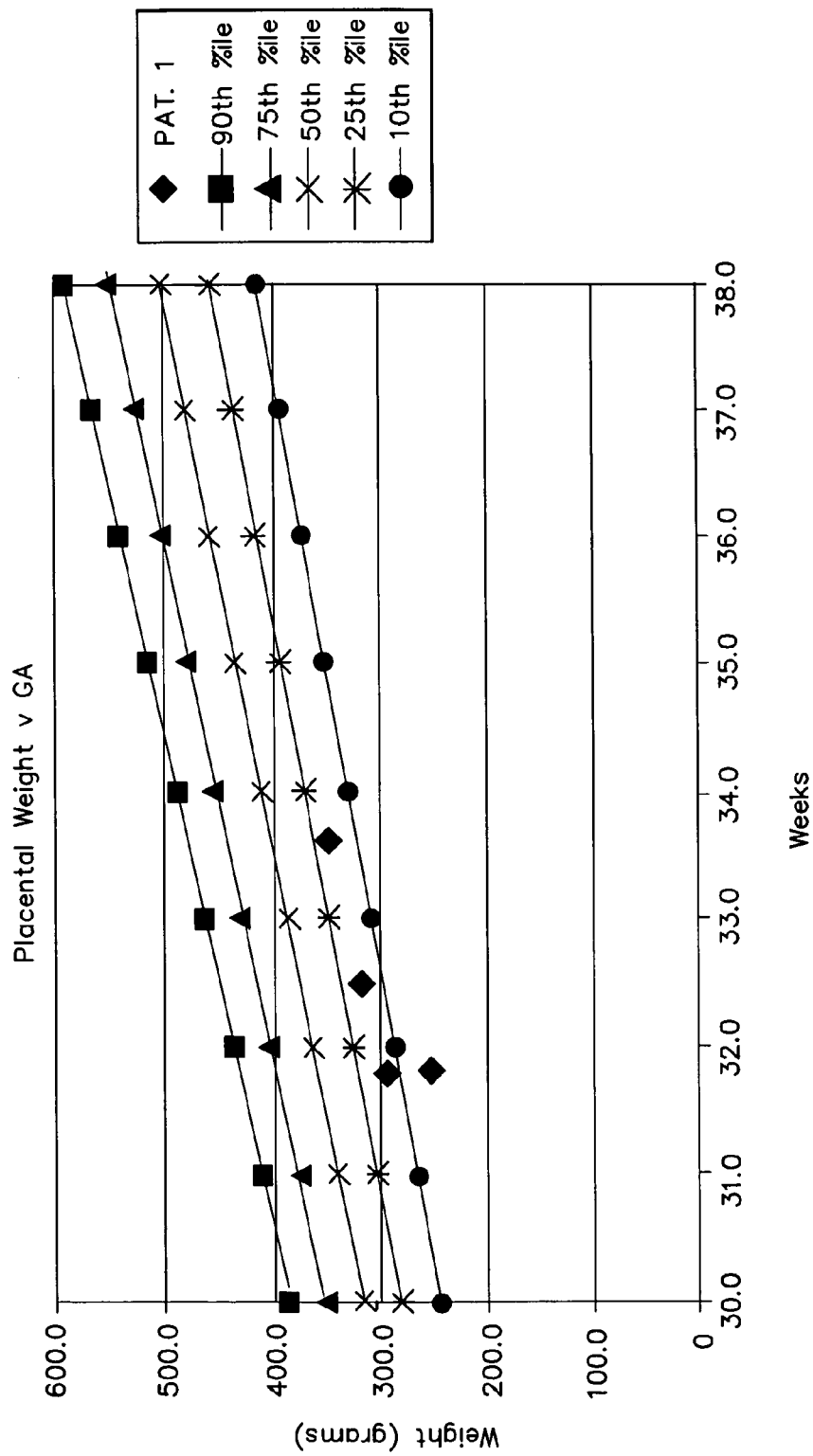
FIG. 5 shows a graph of placental weight versus gestational age employed in one investigation involving a mother (Patient 1) and fetus.

FIG. 5 shows a graph of placental weight versus gestational age employed in one investigation involving a mother (Patient 1) and fetus. At about 30 weeks gestation, the fetus was found to have decreased fetal movement, and a decision was made to determine the placenta volume for the fetus. Placenta volume for Patient 1 (shown by diamond shaped boxes) was initially found to be below the $10^{th}$ percentile for the corresponding gestational age. Two days later, the placenta volume was again measured, and decreased fetal movement and relatively low placenta weight were again found. The patient was admitted to the hospital, for observation, bed rest and fetal monitoring. After increased fluids were administered and bed rest initiated, fetal movement improved and placenta volume was found to track between the $10^{th}$ and $25^{th}$ percentiles (during the 32-34 week gestational age period). The patient was subsequently discharged with instructions for increased fluid intake and bed rest, and was followed with placental weight measurement and other examinations. In this example, the placental weight versus gestational age percentile curves were generated based on data obtained from Pinar et al., Pediatric Pathology & Laboratory Medicine, 16:901-907, 1996 and/or Boyd J D, Hamilton W J, The Human Placenta, Heffer, Cambridge, 1970, but as mentioned above, such curves may be generated in any suitable way.

Figure 6:
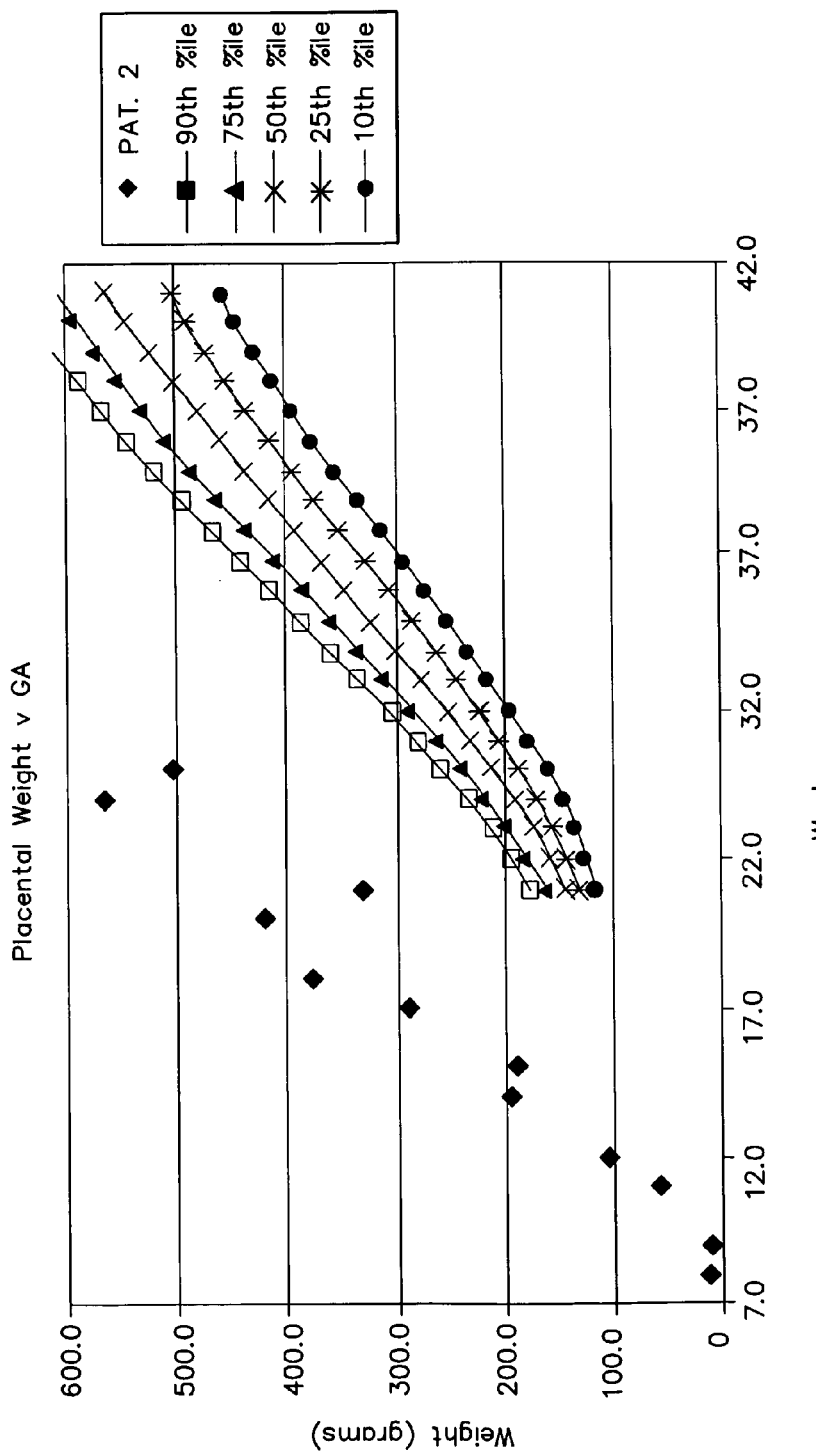
FIG. 6 shows a graph of placental weight versus gestational age employed in one investigation involving a mother (Patient 2) and fetus.

FIG. 6 shows another graph of placental weight versus gestational age employed in another investigation regarding a different mother (Patient 2) than that of FIG. 5. In this investigation, the mother had previously experienced an IUFD and a small placenta volume was found during a post examination. When the mother later became pregnant, she was followed closely with respect to placenta volume starting at approximately 7-8 weeks. FIG. 6 shows her placenta volume compared to placenta growth curves derived from the same data as that of FIG. 5. As can be seen in FIG. 6, the placenta weight for the mother Patient 2 has generally exceeded that of the growth curves, and generally good fetal health has been observed. Thus, this patient likely will not suffer complications due to small placenta during this pregnancy.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for determining a volume of a placenta in utero, the method comprising:
    capturing image information of a placenta in utero including detecting radiation received from the placenta;
    generating, with a computer, a single two-dimensional (2D) image for display based on the detected radiation;
    locating, with the computer, on the single 2D image two points on a peripheral edge of the placenta where at each point on the peripheral edge a convex outer surface of the placenta and a concave inner surface of the placenta join;
    making a height measurement by measuring, with the computer, on the single 2D image the perpendicular distance from a plane defined by the two points on the peripheral edge of the placenta to an apex of the convex surface of the placenta;
    making a thickness measurement, with the computer, by measuring on the single 2D image the largest distance through the placenta between and perpendicular to the convex and concave surfaces, and
    making a maximum width measurement by measuring, with the computer, on the single 2D image the maximum distance between the two points on the peripheral edge; and
    determining, with the computer, a volume of the placenta using the height measurement, the thickness measurement, and the maximum width measurement.

2. The method of claim 1, further comprising:
    assessing a risk of intrauterine fetal demise based on the determined volume of the placenta.

3. The method of claim 1, wherein the radiation is ultrasonic radiation.

4. The method of claim 1, wherein the volume of the placenta is determined using only the measured height, measured thickness, and the measured maximum width of the placenta.

5. The method of claim 1, wherein the step of determining the volume includes:
    selecting one of a plurality of models that each characterize the placenta as having a 3-dimensional convex-concave shape with a height and a thickness; and
    using the selected model to determine the volume of the placenta.

6. A method for assessing fetal health, comprising: capturing image information of a placenta in utero including detecting radiation received from the placenta;
    generating, with a computer, a single two-dimensional (2D) image for display based on the detected radiation;
    locating, with the computer, on the single 2D image two points on a peripheral edge of a convex outer surface of the placenta;
    locating, with the computer, on the single 2D image two points on a peripheral edge of a concave inner surface of the placenta,
    locating, with the computer, on single 2D image two bases, a first base of the two bases joining one of the two points on the peripheral edge of the concave surface to one of the two points on the peripheral edge of the convex surface and a second base of the two bases joining another of the two points on the peripheral edge of the concave surface to another of the two points on the peripheral edge of the convex surface;
    making a height measurement by measuring, with the computer, on the single 2D image the perpendicular distance from a plane defined by the first base and the second base to an apex of the convex surface of the placenta;
    making a thickness measurement and a maximum width measurement, with the computer, wherein:
    the thickness measurement is made by measuring, with the computer, on the single 2D image mage the largest distance through the placenta between and perpendicular to the convex and concave surfaces;
    the maximum width measurement is made by measuring, with the computer, on the single 2D image the maximum distance between the two points on the peripheral edge of the convex outer surface;
    determining, with the computer, a volume of the placenta using the height measurement, the thickness measurement, and the maximum width measurement;
    comparing, with the computer, the volume of the placenta to a plurality of other placenta volumes for other fetuses at a similar gestational age; and
    determining, with the computer, based on the comparison whether the volume of the placenta poses a health risk for the fetus.

7. The method of claim 6, wherein the comparing step comprises: determining whether the volume of the placenta is in a 10th percentile or less of placenta volumes for other fetuses of similar gestational age.

8. The method of claim 7, wherein the comparing step comprises: determining whether the volume of the placenta is in a 5th percentile or less of placenta volumes for other fetuses of similar gestational age.

9. The method of claim 6, wherein the comparing step comprises: determining whether the volume of the placenta is at or sufficiently near a normal growth curve of placenta volume versus gestational age.

10. The method of claim 6, wherein:
    making the height measurement, making the thickness measurement, making the maximum width measurement, and determining the volume of the placenta are performed for a plurality of gestational ages for the fetus to determine a plurality of volumes for the placenta; and
    the comparing includes comparing the plurality of volumes for the placenta to a normal growth curve of placenta volume versus gestational age to determine whether a growth trend for the placenta is similar to the normal growth curve.

11. The method of claim 6, further comprising: administering treatment for the fetus and mother if a health risk is presented by the volume of the placenta.

12. The method of claim 6, wherein the comparing step comprises: determining whether the placenta is in the 90th percentile or more of placenta volumes for other fetuses of the same gestational age.

13. A method for determining a volume of a placenta in utero, the method comprising:
    capturing image information of a placenta in utero including detecting radiation received from the placenta;

generating, with a computer, a single two-dimensional (2D) image for display based on the detected radiation;

locating, with the computer, on the single 2D image two points on a peripheral edge where at each point on the peripheral edge a maternal surface of the placenta and a fetal surface of the placenta join, making a height measurement by measuring, with the computer, on the single 2D image the perpendicular distance from a plane defined by the two points on the peripheral edge to an apex of the maternal surface, making a thickness measurement by measuring, with the computer, on the single 2D image the largest distance through the placenta between and perpendicular to the maternal and fetal surfaces, and making a maximum width measurement by measuring, with the computer, on the single 2D image the maximum distance between the two points on the peripheral edge; and determining, with the computer, a volume of the placenta using the height measurement, the thickness measurement, and the maximum width measurement.

14. The method of claim 13, further comprising: assessing a risk of intrauterine fetal demise based on the determined volume of the placenta.

15. The method of claim 13, wherein the radiation is ultrasonic radiation.

16. The method of claim 13, wherein the volume of the placenta is determined using only the height measurement, thickness measurement, and the maximum width measurement.

17. The method of claim 13, wherein determining the volume includes:

selecting one of a plurality of models that each characterize the placenta as having a 3-dimensional convex-concave shape with a height and a thickness; and using the selected model to determine the volume of the placenta.

* * * * *